US00PP31753P2

(12) United States Plant Patent
Jones

(10) Patent No.: US PP31,753 P2
(45) Date of Patent: May 12, 2020

(54) ***IPOMOEA* PLANT NAMED 'ISGBR03-1'**

(50) Latin Name: *Ipomoea batatas*
Varietal Denomination: ISGBR03-1

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/501,767

(22) Filed: Jun. 4, 2019

(51) Int. Cl.
*A01H 5/06* (2018.01)
*A01H 5/12* (2018.01)
*A01H 6/00* (2018.01)

(52) U.S. Cl.
USPC ..... Plt./258
CPC ..... *A01H 6/00* (2018.05)

(58) Field of Classification Search
USPC ..... Plt./258, 263.1, 226
CPC ..... A01H 5/02; A01H 5/06; A01H 5/12
See application file for complete search history.

*Primary Examiner* — Kent L Bell
(74) *Attorney, Agent, or Firm* — Cassandra Bright

(57) ABSTRACT

A new and distinct *Ipomoea batatas* cultivar named 'ISGBR03-1' is disclosed, characterized by purple-bronze palmate shaped foliage. Plants are semi-compact, have dense foliage, and produce many lateral branches. The new cultivar is an *Ipomoea batatas*, typically suited for ornamental container and garden use.

2 Drawing Sheets

Latin name of the genus and species: *Ipomoea batatas*.
Variety denomination: 'ISGBR03-1'.

BACKGROUND OF THE INVENTION

The new variety originated as a chance discovery by the inventor, Steve Jones. The variety was discovered as a naturally occurring whole plant mutation from an unnamed, unpatented proprietary variety of *Ipomoea batatas*. The new variety was discovered in August 2018 at a commercial greenhouse in Santa Paula, Calif.

After selecting and isolating the new cultivar, asexual reproduction of the new variety 'ISGBR03-1' was first performed by vegetative tip cuttings in a commercial greenhouse in Santa Paula, Calif. in October 2018. 'ISGBR03-1' has since produced several generations and has shown that the unique features of this cultivar are stable and reproduced true to type. Typical asexual reproduction of the new variety is by vegetative tip cuttings.

SUMMARY OF THE INVENTION

The cultivar 'ISGBR03-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ISGBR03-1'. These characteristics in combination distinguish 'ISGBR03-1' as a new and distinct *Ipomoea* cultivar:

1. Vigorous growth rate.
2. Distinct purple-bronze foliage color.
3. Semi-compact, mounding habit.
4. Dense foliage.
5. Very well branched.

PARENTAL COMPARISON

Plants of the new cultivar 'ISGBR03-1' are similar to the parent in most horticultural characteristics. However, 'ISGBR03-1' differs in the following:

1. The new variety has thinner, more elongated leaves than the parent.

COMMERCIAL COMPARISON

Plants of the new cultivar 'ISGBR03-1' can be compared to the commercial variety *Ipomoea batatas* 'Sweet Caroline Bronze', U.S. Plant Pat. No. 15,437. Plants of 'ISGBR03-1' are similar to plants of 'Sweet Caroline Bronze' in some horticultural characteristics, however, plants of 'ISGBR03-1' differ in the following:

1. The new variety has a more vigorous growth rate than this comparator.
2. The new variety has more reduced lobing than this comparator.

BRIEF DESCRIPTION OF THE PHOTOGRAPHS

Figure 1:
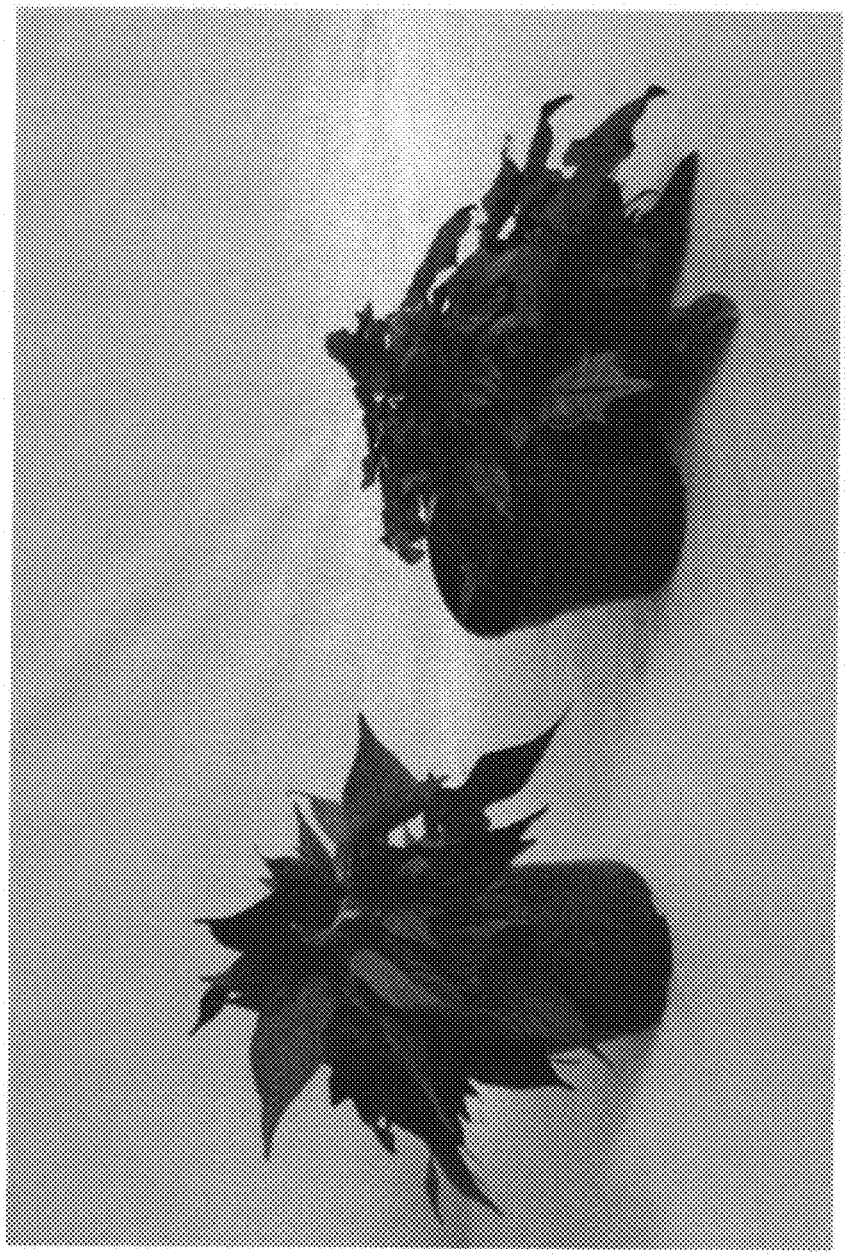

The accompanying photograph in FIG. 1 illustrates in full color a typical plant of 'ISGBR03-1', seen in the left side of the photograph. The plant on the right of the photograph is the abovementioned comparator variety 'Sweet Caroline Bronze'. Both plants are approximately 8 weeks old, from an unrooted cutting, shown in a 6 inch pot.

Figure 2:
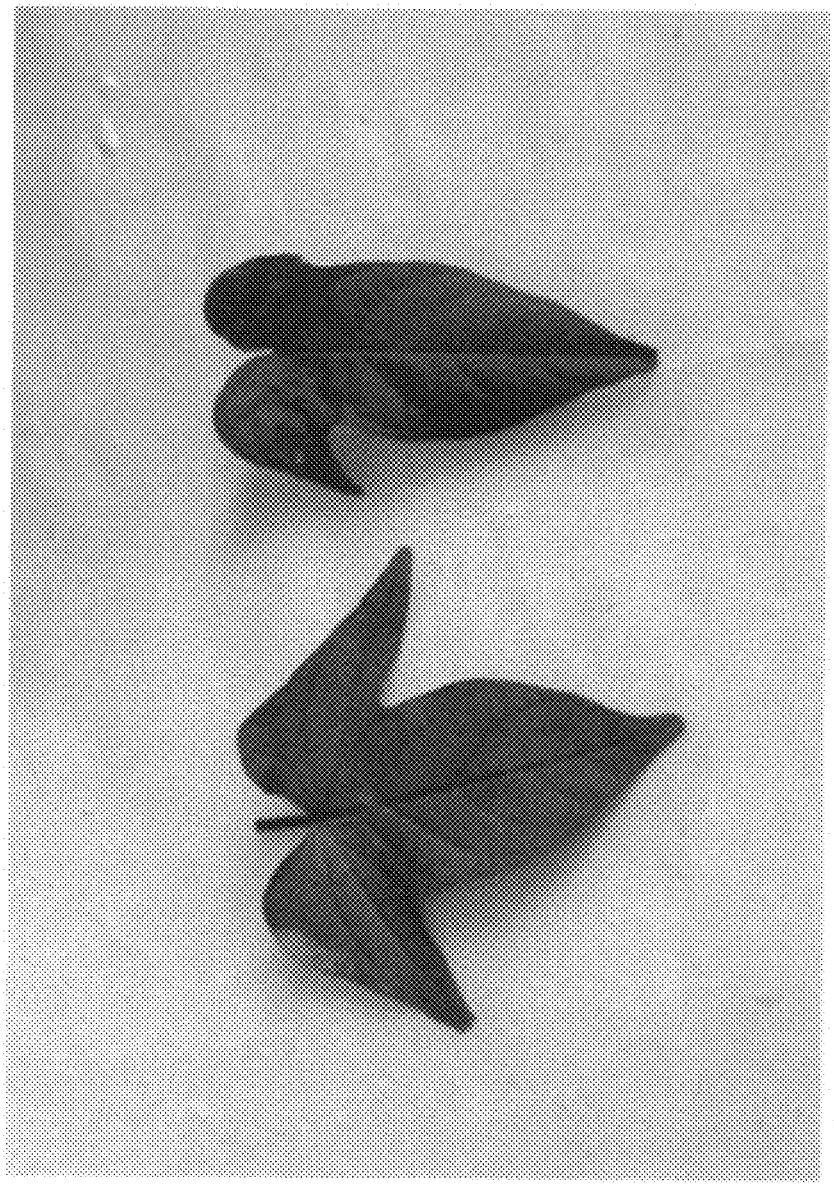

FIG. 2 illustrates a close up of the foliage of both the new variety and the abovementioned comparator. Foliage of the new variety is on the right in FIG. 2, foliage of this comparator is seen on the left side of the photograph.

Plants were grown in a greenhouse in Santa Paula, Calif. The photographs were taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2007, except where general terms of ordinary dictionary significance are used. The following observations and measurements describe 'ISGBR03-1' plants grown during the Spring months in a greenhouse in Santa Paula, Calif., under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea batatas* 'ISGBR03-1'.

Age of the plant described: Approximately 8 weeks from an unrooted cutting.

Container size of the plant described: 1 gallon commercial container.

Propagation:

*Propagation method.*—Terminal cuttings.

*Time to develop roots suitable for transplanting.*—Summer — about 6 days at an average temperature of 24° C.; Winter — about 10 days at an average temperature of 24° C.

*Root description.*—Thick, fleshy. Roots colored closest to RHS Yellow-White 158A.

*Tuber description.*—Not observed to date.

Plant:

*Growth habit.*—Semi-compact, and mounding. Dense and bushy.

*Height.*—Measured from top of soil line of pot, approximately 22 cm.

*Plant spread.*—Approximately 35 cm.

*Growth rate.*—Rapid.

*Branching characteristics.*—Very free branching, alternate or whorled occurring.

Primary lateral branches:

*Length.*—7 to 12 cm.

*Diameter.*—Approximately 0.5 cm.

*Texture.*—Glabrous.

*Color.*—Near RHS Greyed-Purple 187B.

*Strength.*—Strong.

*Internode length.*—0.5-1.0 cm.

*Adventitious roots at nodes.*—Not observed.

Secondary lateral branches:

*Length.*—4 to 8 cm.

*Diameter.*—Approximately 0.4 cm.

*Texture.*—Glabrous.

*Color.*—Near RHS Purple N79B.

*Strength.*—Flexible.

*Internode length.*—0.4 to 1.0 cm.

*Quantity per 8 week old plant.*—Approximately 25.

*Adventitious roots at nodes.*—Not observed.

New shoot growth characteristics:

*Color.*—Near RHS Purple N79B.

*Aspect.*—Upright in the center, outward on outer circumference of plant.

*Texture.*—Glabrous.

Foliage:

Leaf:

*Arrangement.*—Whorled and alternate, simple.

*Average length.*—11 cm.

*Average width.*—9 cm.

*Shape of blade.*—Cordate with 2 sinuses, approximately 2 cm deep.

*Apex.*—Acute to acuminate.

*Base.*—Cordate.

*Margin.*—Entire.

*Aspect.*—Upward fold or slightly undulate.

*Texture of top surface.*—Glabrous.

*Texture of bottom surface.*—Glabrous.

*Appearance of top surface.*—Matte.

*Appearance of bottom surface.*—Matte.

*Quantity of leaves per lateral branch.*—Average 10 to 18.

Foliage color:

*Young foliage upper side.*—Near RHS Yellow-Green 147B with complete overlay Purple N79C mixed with Greyed-Purple 183B. Veins Greyed-Purple N186D.

*Young foliage under side.*—Near RHS Yellow-Green 147C lightly mottled N186D. Veins Purple N79D.

*Mature foliage upper side.*—Background hue near RHS Yellow-Green 147B, complete overlay of Purple N79A and N79B. Veins Purple 79C.

*Mature foliage under side.*—Background hue near RHS Yellow-Green 147B, strong overlay of Greyed-Purple N186C. Veins Purple 79B.

Venation:

*Type.*—Palmate, reticulate.

Petiole:

*Length.*—Approximately 3 to 7 cm.

*Diameter.*—Approximately 0.3 cm at base, 0.2 cm at leaf attachment.

*Texture.*—Glabrous.

*Color.*—Near RHS Purple N79B.

*Strength.*—Strong.

*Aspect.*—Straight to slightly curved.

Flower: Flowering not observed to date.

Other characteristics:

Seeds and fruits: No seeds or fruits observed to date.

Disease/pest resistance: Neither resistance nor susceptibility to the normal pests and diseases of *Ipomoea* has been observed.

Temperature tolerance: Tolerates low temperatures to approximately 2° C. Good high temperature tolerance, observed to at least 38° C.

What is claimed is:

1. A new and distinct cultivar of *Ipomoea batatas* plant named 'ISGBR03-1' as herein illustrated and described.

* * * * *